United States Patent [19]

Matsuyama et al.

[11] Patent Number: 5,401,660

[45] Date of Patent: * Mar. 28, 1995

[54] PROCESS FOR PRODUCING OPTICALLY ACTIVE 1,3-BUTANEDIOL BY ASYMMETRIC ASSIMILATION

[75] Inventors: Akinobu Matsuyama; Teruyuki Nikaido; Yoshinori Kobayashi, all of Niigata, Japan

[73] Assignee: Daicel Chemical Industries, Ltd., Osaka, Japan

[*] Notice: The portion of the term of this patent subsequent to Jun. 15, 2010 has been disclaimed.

[21] Appl. No.: 964,264

[22] Filed: Oct. 21, 1992

Related U.S. Application Data

[62] Division of Ser. No. 449,929, Dec. 7, 1989, Pat. No. 5,219,757.

[30] Foreign Application Priority Data

Apr. 27, 1988 [JP] Japan ................. 63-105024
Apr. 27, 1988 [JP] Japan ................. 63-105025
Apr. 27, 1988 [JP] Japan ................. 63-105026
Sep. 8, 1988 [JP] Japan ................. 63-225078
Oct. 7, 1988 [JP] Japan ................. 63-253019

[51] Int. Cl.⁶ ............................. C12P 41/00
[52] U.S. Cl. ........................ 435/280; 435/822; 435/911

[58] Field of Search ............... 435/280, 822, 911

[56] References Cited

FOREIGN PATENT DOCUMENTS 224246 11/1986 European Pat. Off. .
204187 of 1983 Japan .
191361 of 1986 Japan .
1320977 3/1990 Japan .

OTHER PUBLICATIONS

Levene et al., J. Biol. Chem., 94, pp. 361–366, (1931).
Neuberg et al., Biochem. Z., 92, pp. 96–110 (1918).
Murakami et al., Bulletin of the Chemical Society of Japan, vol. 53, No. 5, pp. 1356–1360, (1980).

*Primary Examiner*—Douglas W. Robinson
*Assistant Examiner*—S. Saucier
*Attorney, Agent, or Firm*—Birch, Stewart, Kolasch & Birch

[57] ABSTRACT

An optically active 1,3-butanediol can be produced by either (1) treating a mixture of 1,3-butanediol enantiomers with a microorganism, which has been optionally treated, capable of asymmetrically assimilating said mixture, or (2) preparing a microorganism, which has been optionally treated, capable of asymmetrically reducing 4-hydroxy-2-butanone, and collecting optically active 1,3-butanediol.

13 Claims, No Drawings

PROCESS FOR PRODUCING OPTICALLY ACTIVE 1,3-BUTANEDIOL BY ASYMMETRIC ASSIMILATION

This application is a divisional of application Ser. No. 07/449,929, filed on Dec. 7, 1989, now U.S. Pat. No. 5,219,757, the entire contents of which are hereby incorporated by reference.

FIELD OF INDUSTRIAL APPLICATION

The present invention relates to a process for producing optically active 1,3-butanediol with a microorganism.

Optically active 1,3-butanediol is an important starting material for various medicines such as antibiotics.

PRIOR ART

Known processes for producing optically active 1,3-butanediol include (1) a process wherein a chemically synthesized mixture of 1,3-butanediol racemates is optically resolved with an optical resolving agent (cf. Japanese Patent Laid-Open No. 191631/1986) and (2) a process wherein it is produced from 4-hydroxy-2-butanone by asymmetric synthesis with a Raney nickel catalyst treated with an optically active compound [cf. Japanese Patent Laid-Open No. 204187/1983 and Bull. Chem. Soc. Jpn., 53, 1356 to 1360 (1980)]. However, both the processes (1) and (2) have a defect that expensive optical resolving agent and catalyst must be used and, in addition, the product obtained by the process (2) has a low optical purity. Under these circumstances, it is demanded to establish a process for producing optically active 1,3-butanediol having a high optical purity in an economically advantageous and convenient manner.

DISCLOSURE OF THE INVENTION

The present invention provides a process for producing optically active 1,3-butanediol which comprises either (1) treating a mixture of 1,3-butanediol enantiomers with a microorganism, which has been optionally treated, capable of asymmetrically assimilating said mixture, or (2) preparing a microorganism, which has been optionally treated, capable of asymmetrically reducing 4-hydroxy-2-butanone, and collecting optically active 1,3-butanediol.

The present invention involves (1) asymmetric assimilation and (2) reduction as follows:. (1) a process for producing optically active 1,3-butanediol which comprises treating a mixture of 1,3-butanediol enantiomers with a microorganism, which has been optionally treated, capable of asymmetrically assimilating said mixture and collecting optically active 1,3-butanediol remaining intact, and (2) a process for producing optically active 1,3-butanediol which comprises treating 4-hydroxy-2-butanone with a microorganism, which has been optionally treated, capable of asymmetrically reducing 4-hydroxy-2-butane into either (R)-1,3-butanediol or (S)-1,3-butanediol and collecting the (R)-1,3-butanediol or (S)-1,3-butanediol thus formed.

The present invention will now be described in detail by referring to these two processes.

(1) Asymmetric Assimilation

After intensive investigations made for the purpose of getting a microorganism usable for producing optically active 1,3-butanediol having a high optical purity by asymmetric assimilation, the inventors have found that a microorganism selected from among those belonging to the genera Brevibacterium, Candida, Enterobacter, Geotrichum, Klebsiella, Lodderomyces, Pseudomonas, Rhodotorula, Saccharomyces, Saccharomycopsis, Sterigmatomyces and Trichosporon is capable of asymmetrically assimilating a mixture of 1,3-butanediol enantiomers to leave (R)-1,3-butanediol intact, and that a microorganism selected from among those belonging to the genera Agrobacterium, Azotobacter, Bacillus, Brettanomyces, Candida, Citrobacter, Corynebacterium, Dekkera, Endomyces, Erwinia, Hansenula, Issatchenkia, Klebsiella, Kluyveromyces, Geotrichum, Micrococcus, Mycobacterium, Pachysolen, Paracoccus, Pichia, Protaminobacter, Pseudomonas, Saccharomyces, Saccharomycopsis, Selenotila, Serratia, Stephanoascus and Xanthomonas is capable of asymmetrically assimilating a mixture of 1,3-butanediol enantiomers to leave (S)-1,3-butanediol intact.

The microorganism usable in the present invention may be any of those belonging to the genus Brevibacterium, Candida, Enterobacter, Geotrichum, Klebsiella, Lodderomyces, Pseudomonas, Rhodotorula, Saccharomyces, Saccharomycopsis, Sterigmatomyces or Trichosporon capable of asymmetrically assimilating a mixture of 1,3-butanediol enantiomers to leave (R)-1,3-butanediol intact or any of those belonging to the genus Agrobacterium, Azotobacter, Bacillus, Brettanomyces, Candida, Citrobacter, Corynebacterium, Dekkera, Endomyces, Erwinia, Hansenula, Issatchenkia, Klebsiella, Kluyveromyces, Geotrichum, Micrococcus, Mycobacterium, Pachysolen, Paracoccus, Pichia, Protaminobacter, Pseudomonas, Saccharomyces, Saccharomycopsis, Selenotila, Serratia, Stephanoascus or Xanthomonas capable of asymmetrically assimilating a mixture of 1,3-butanediol enantiomers to leave (S)-1,3-butanediol intact.

The microorganisms capable of asymmetrically assimilating a mixture of 1,3-butanediol enantiomers to leave (R)-1,3-butanediol intact include *Brevibacterium iodinum* IFO 3558, *Candida rugosa* IFO 1364, *Candida parapsilosis* IFO 0640, *Candida parapsilosis* IFO 0708, *Candida parapsilosis* IFO 1396, *Enterobacter cloacac* ATCC 7256, *Geotrichum candidum* IFO 4601, *Geotrichum candidum* IFO 5767, *Geotrichum candidum* IFO 5368, *Geotrichum rectangulatum* JCM 1750, *Geotrichum klebahnii* JCM 2171, *Geotrichum fermentans* JCM 2467, *Geotrichum capitatum* JCM 3908, *Geotrichum eriense* JCM 3912, *Klebsiella pneumoniae* IFO 12019, *Lodderomyces elongisporus* IFO 1676, *Psudomonas diminuta* IFO 12697, *Rhodotorula glutinis* IFO 0395, *Saccharomyces cerevisiae* AHU 3402, *Saccharomycopsis lipolytica* ITO 1550, *Sterigmatomyces elviae* DSM 70852, *Trichosporon cutaneum* IFO 1198 and *Trichosporon capitatum* IFO 0743.

The microorganisms capable of asymmetrically assimilating a mixture of 1,3-butanediol enantiomers to leave (S)-1,3-butanediol intact include *Agrobacterium radiobacter* IFO 12664, *Azotobacter chroococcum* IFO 12994, *Bacillus brevis* IFO 3331, *Bacillus cereus* AHU 1707, *Bacillus cereus* AHU 1355, *Bacillus sphaericus* IFO 3525, *Bacillus sphaericus* IFO 3341, *Bacillus subtilis* IFO 3007, *Bacillus subtilis* IFO 3037, *Brettanomyces abstines* DSM 70726, *Candida cariosilignicola* DSM 2148, *Candida kefyr* (Beijerinck) DSM 70073, *Candida krusei* (Castellani) DSM 70025, *Candida succiphila* DSM 2149, *Candida utilis* IFO 0639, *Candida utilis* IFO 0626, *Citrobacter freundii* AHU 1534, *Corynebacterium glutamicum* ATCC 13032, *Corynebacterium michiganense* IFO 13762, *Dekkera bruxellensis* IFO 1590, *Endomyces decipien* IFO 0102, *Erwinia carotovora* subsp. *carotovora* IFO 3830, *Geotrichum fragrans* JCM 1749, *Hansenula anomala* DSM 70130, *Hansenula minuta* DSM 70274, *Hansenula subpelliculosa* IFO 0808, *Hansenula wickerhamii* DSM 70280, *Hansenula wingel* DSM 10281, *Issatchenkia scutulata* var. *scutulata* IFO 10070, *Klebsiella pneumoniae* IFO 12059, *Kluyveromyces drosophilarum* IFO 1012, *Kluyveromyces lactis* IFO 1267, *Kluyveromyces lactis* IFO 1903, *Micrococcus luteus* IFO 3333, *Micrococcus roseus* IFO 3764, *Mycobacterium smegmatis* IFO 3153, *Pachysolen tannophilus* IFO 1007, *Paracoccus denitrificans* IFO 12442, *Pichia cellobiosa* DSM 2147, *Pichia farinosa* IFO 1163, *Pichia heedii* IFO 10020, *Pichia heedii* IFO 10019, *Pichia lindnerii* DSM 70718, *Pichia opuntiae* var. *thermotolerans* IFO 10026, *Pichia opuntiae* var. *thermotolerans* IFO 10025, *Pichia pastoris* DSM 70382, *Pichia querquum* DSM 70386, *Pichia sargentensis* DSM 70388, *Pichia trehalophia* DSM 70391, *Protaminobacter ruber* IAM 1081, *Pseudomonas acidovorans* IFO 13582, *Pseudomonas diminuta* IFO 12697, *Pseudomonas fluorescens* IFO 12055, *Pseudomonas fluorescens* IFO 3081, *Pseudomonas putida* IFO 3738, *Saccharomyces cerevisiae* IAM 0216, *Saccharomycopsis fibuligera* IFO 0103, *Selenotila peltata* DSM 70579, *Serratia marcescens* IAM 1105, *Stephanoascus ciferrii* IFO 1854, *Xanthomonas maltophilia* IFO 12690 and *Xanthomonas oryzae* IAM 1657.

Each strain may be either a wild type, a variant or a recombinant obtained by genetic engineering such as cell fusion or gene recombination.

Microorganisms having IFO numbers assigned thereto are described in the List of Cultures, 8th ed., vol. 1 (1988) published by the Institute for Fermentation, Osaka (IFO) and available therefrom. Those having AHU numbers are described in the Catalogue of Cultures, 4th ed. (1987) published by Japan Federation of Culture Collection (JFCC) and available from the Faculty of Agriculture, Hokkaido University. Those having ATCC numbers are described in the Catalogue of Bacteria Phages rDNA Vectors, 16th ed. (1985) published by American Type Culture Collection (ATCC) and available therefrom. Those having JMC numbers are described in the Catalogue of Strains, 3rd ed. (1986) published by Japan Cellection of Microorganisms, RIKEN and available therefrom. Those having IAM numbers are available from the Institute of Applied Microbiology, the University of Tokyo. Those having DSM numbers are described in the Catalog of Strains (1983) published by Deutsche Sammlung von Mikroorganismen (DSM) and available therefrom.

The following strains were deposited at the Institute for Fermentation, Osaka, 17-85 Juso-honmachi 2-chome, Yodogawa-ku, Osaka Japan as indicated:

| Strain | Accession Number | Deposit Date |
|---|---|---|
| *Kluveromyces lactis* | IFO 1267 | Dec. 9, 1964 |
| *Pichia opuntiae* | IFO 10025 | Mar. 19, 1982 |
| *Geotricum candidum* | IFO 5368 | 1952 |
| *Candida utilis* | IFO 0639 | 1954 |
| *Candida parapsilosis* | IFO 1396 | June 1, 1967 |
| *Brevibacterium iodinium* | IFO 3558 | May 30, 1957 |
| *Xanthomonas maltophilia* | IFO 12690 | July 31, 1968 |
| *Stephanoascus ciferrii* | IFO 1854 | Aug. 23, 1977 |
| *Paracoccus denitrificans* | IFO 12442 | Sept. 15, 1966 |
| *Pachysolen tannophilus* | IFO 1007 | Aug. 24, 1954 |
| *Mycobacterium smegmatis* | IFO 3153 | Sept. 17, 1952 |
| *Micrococcus luteus* | IFO 3333 | Aug. 24, 1954 |
| *Klebsiella pneumoniae* | IFO 12059 | Sept. 9, 1964 |
| *Issatchenkia scutulata* var. *scutulata* | IFO 10070 | Jan. 14, 1983 |
| *Hansenula subpelliculosa* | IFO 0808 | Nov. 13, 1956 |
| *Erwinia cartovora* subsp. *cartovora* | IFO 3830 | Oct. 12, 1959 |
| *Endomyces decipiens* | IFO 0102 | 1946 |
| *Dekkera bruxellensis* | IFO 1590 | May 6, 1971 |
| *Corynebacterium michiganese* | IFO 13762 | Sept. 19, 1977 |
| *Bacillus subtilis* | IFO 3007 | 1946 |
| *Azotobacter chroococcum* | IFO 12994 | July 1, 1969 |
| *Agrobacterium radiobacter* | IFO 12664 | July 31, 1968 |
| *Trichosporon cutaneum* | IFO 1198 | Sept. 6, 1963 |
| *Saccharomycopsis lipolytica* | IFO 1550 | May 27, 1970 |
| *Rhodotorula glutinis* | IFO 0395 | 1941 |
| *Pseudomonas diminuta* | IFO 12697 | July 31, 1968 |
| *Lodderomyces elongisporus* | IFO 1676 | Dec. 17, 1975 |
| *Klebsiella pneumoniae* | IFO 12009 | May 25, 1963 |
| *Pseudomonas putida* | IFO 3738 | June 21, 1958; |

In addition, a culture of *Serratia marcescens*, assigned the accession number IAM 1105, was deposited at the Institute of Applied Microbiology, at the University of Tokyo, Japan, prior to Dec. 25, 1992.

The above deposits were made as to afford a permanently viable stock of, and ready public accessibility to, the indicated strains so as to allow practice of the invention described in this patent document. Samples of each of these strains will be made available to the public (1) for the term of 30 years, (2) for five years after the last request for a sample of a deposited strain or (3) for the enforceable life of any patent which issues from this document, whichever is longer.

The culture medium used in the present invention is not particularly limited so far as the microorganism can grow in or on it. The carbon source may be any of carbon nutrients for growing the microorganism. The carbon sources include, for example, saccharides such as glucose, fructose, sucrose and dextrin; alcohols such as sorbitol, ethanol and glycerol; organic acids such as fumaric, citric, acetic and propionic acids and salts thereof; hydrocarbons such as paraffin; and mixtures of them. The nitorgen sources include inorganic and organic nitrogenous compounds such as ammonium salts of inorganic acids, e.g., ammonium chloride, ammonium sulfate and ammonium phosphate; ammonium salts of organic acids, e.g., ammonium fumarate and ammonium citrate; meat extract; yeast extract; corn steep liquor; casein hydrolyzate; urea as well as mixtures thereof. Furthermore various nutritional sources commonly used in the culture of microorganisms, such as inorganic salts, trace metal salts and vitamins, may be appropriately mixed and used in the present invention. In addition, materials effective in promoting the growth of the microorganism, in elevating the productivity of the target compound of the present invention or in maintaining the pH value of the medium on the desired level may be added, if required.

The pH value of the medium may be adjusted to 3.0 to 9.5, preferably 4 to 8. The culture may be carried out at a temperature of 20° to 45° C., preferably 25° to 37° C., either aerobically or anaerobically under conditions suitable for the growth of the microorganism for 5 to 120 hours, preferably about 12 to 72 hours.

The asymmetric assimilation may be effected by using the culture medium as such. Alternately, the cells may be separated by, for example, centrifugation, optionally washed and resuspended in a buffer solution or water. Then the mixture of 1,3-butanediol enantiomers may be added to the suspension thus obtained. In this reaction, it is sometimes preferable to add a carbon source such as glucose or sucrose to the medium to thereby supply energy. The cells may be used as such in the form of viable cells. Alternately, they may be ground, treated with acetone or lyophilized. These cells, which have been optionally treated, may be immobilized prior to the use by a conventional method such as the polyacrylamide gel, sulfur-containing polysaccharide gel (such as carrageenan gel), alginic acid gel or agar gel method. Furthermore, an enzyme obtained from said treated cells by combining known methods may be used in the present invention.

The mixture of 1,3-butanediol enantiomers may be added either at once at the initiation of the reaction or in portions in the course of the reaction either as such, dissolved in water or an inert organic solvent or dispersed in, for example, a surfactant.

The reaction may be conducted at a pH value of 3 to 10, preferably 5 to 9, at 10° to 60° C., preferably 20° to 40° C. for 1 to 120 hours with or without stirring. A prolonged reaction time causes a reduction in the amount of the remaining 1,3-butanediol, though an optically active 1,3-butanediol having a high optical purity can be obtained in this case. The concentration of the substrate may range preferably from about 0.1 to 10%, though it is not restricted thereto.

The optically active 1,3-butanediol remaining intact after the reaction can be easily collected by extracting the reaction mixture, from which the cells have been optionally separated, with an organic solvent and purifying the extract by, for example, distillation or column chromatography.

(2) Reduction

After intensive investigations made for the purpose of getting a microorganism usable for producing optically active 1,3-butanediol having a high optical purity by asymmetric reduction, the inventors have found that a microorganism selected from among those belonging to the genera Ambrosiozyma, Bacillus, Candida, Citrobacter, Corynebacterium, Hansenula, Issatchenkia, Kluyveromyces, Pichia, Protaminobacter, Pseudomonas, Rhodotorula, Selenotila, Schizosaccharomyces, Stephanoascus and Xanthomonas is capable of asymmetrically reducing 4-hydroxy-2-butanone into (R)-1,3-butanediol, and that a microorganism selected from among those belonging to the genera Brevibacterium, Candida, Geotrichum, Klebsiella, Lodderomyces, Saccharomycopsis and Trichosporon is capable of asymmetrically reducing 4-hydroxy-2-butanone into (S)-1,3-butanediol.

The microorganism usable in the present invention may be any of those belonging to the genus Ambrosiozyma, Bacillus, Candida, Citrobacter, Corynebacterium, Hansenula, Issatchenkia, Kluyveromyces, Pichia, Protaminobacter, Pseudomonas, Rhodotorula, Selenotila, Schizosaccharomyces, Stephanoascus or Xanthomonas capable of asymmetrically reducing 4-hydroxy-2-butanone into (R)-1,3-butanediol or any of those belonging to the genus Brevibacterium, Candida, Geotrichum, Klebsiella, Saccharomycopsis or Trichosporon capable of asymmetrically reducing 4-hydroxy-2-butanone into (S)-1,3-butanediol.

The microorganisms capable of forming (R)-1,3-butanediol from 4-hydroxy-2-butanone include *Ambrosiozyma cicatricosa* IFO 1846, *Bacillus sereus* AHU 1355, *Bacillus subtilis* IFO 3007, *Candida cariosilignicola* DSM 2148, *Candida arborea* IAM 4147, *Candida kefyr* (Beijerinck) DSM 70073, *Candida krusei* (Castellani) DSM 70075, *Candida guilliermondii* IAM 4412, *Candida succiphila* DSM 2149, *Candida utilis* IFO 0639, *Candida utilis* IFO 0626, *Candida utilis* IAM 4277, *Citrobacter freundii* AHU 1534, *Corynebacterium michiganense* IFO 13762, *Hansenula polymorpha* ATCC 26012, *Hansenula minuta* DSM 70274, *Hansenula subpelliculosa* IFO 0808, *Hansenula fabianii* IFO 1254, *Hansenula wickerhamii* DSM 70280, *Hansenula wingei* DSM 10281, *Issatchenkia scutulata* var. *scutulata* IFO 10070, *Issatchenkia scutulata* var. *scutulata* IFO 10069, *Kluyveromyces drosophilarum* IFO 1012, *Kluyveromyces lactis* IFO 1267, *Kluyveromyces lactis* IFO 1903, *Pichia cellobiosa* DSM 2147, *Pichia heedii* IFO 10019, *Pichia heedii* IFO 10020, *Pichia lindnerii* DSM 70718, *Pichia opuntiae* var. *thermotolerans* IFO 10025, *Pichia pastoris* DSM 70382, *Pichia trehalophia* DSM 70391, *Protaminobacter ruber* IAM 1081, *Pseudomonas diminuta* IFO 12697, *Pseudomonas fluorescens* IFO 3081, *Pseudomonas putida* IFO 3738, *Rhodotorula rubra* IFO 0383, *Selenotila peltata* DSM 70579, *Schizosaccharomyces pombe* IFO 0363, *Stephanoascus ciferrii* IFO 1854 and *Xanthomona maltophilia* IFO 12690. The microorganisms capable of forming (S)-1,3-butanediol from 4-hydroxy-2-butanone include *Brevibacterium iodinum* IFO 3558, *Candida rugosa* IFO 1664, *Candida parapsilosis* IFO 0640, *Candida parapsilosis* IFO 0708, *Candida parapsilosis* IFO 1396, *Geotrichum candidum* IFO 4601, *Geotrichum candidum* IFO 5767, *Geotrichum candidum* IFO 5368, *Geotrichum rectangulatum* JCM 1750, *Geotrichum klebanoii* JCM 2171, *Geotrichum fermentans* JCM 2467, *Geotrichum capitatum* JCM 3908, *Geotrichum eriense* JCM 3912, *Klebsiella pneumoniae* IFO 12019, *Lodderomyces elongisporus* IFO 1676, *Saccharomycopsis lipolytica* ITO 1550, *Trichosporon cutaneum* IFO 1198 and *Trichosporon capitatum* IFO 0743.

Each strain may be either a wild type, a variant or a recombinant obtained by genetic engineering such as cell fusion or gene recombination.

Microorganisms having IFO numbers assigned thereto are described in the List of Cultures, 8th ed., vol. 1 (1988) published by the Institute for Fermentation, Osaka (IFO) and available therefrom. Those having AHU numbers are described in the Catalogue of Cultures, 4th ed. (1987) published by Japan Federation of Culture Collection (JFCC) and available from the Faculty of Agriculture, Hokkaido University. Those having JCM numbers are described in the Catalogue of Strains, 3rd ed. (1986) published by Japan Collection of Microorganisms, RIKEN and available therefrom. Those having ATCC numbers are described in the Catalogue of Bacteria Phages rDNA Vectors, 16th ed. (1985) and the Catalogue of Fungi/Yeast, 17th ed. (1987) published by American Type Culture Collection (ATCC) and available therefrom. Those having DSM numbers are described in the Catalog of Strains (1983) published by Deutsche Sammlung von Mikroorganismen (DSM) and available therefrom. Those having IAM numbers are available from the Institute of Applied Microbiology, the University of Tokyo.

The culture medium used in the present invention is not particularly limited so far as the microorganism can grow in or on it. The carbon source may be any of carbon nutrients for growing the microorganism. The carbon sources include, for example, saccharides such as glucose, fructose, sucrose and dextrin; alcohols such as sorbitol, ethanol and glycerol; organic acids such as fumaric, citric, acetic and propionic acids and salts thereof; hydrocarbons such as paraffin; and mixtures of them. The nitrogen sources include inorganic and organic nitrogenous compounds such as ammonium salts of inorganic acids, e.g. ammonium chloride, ammonium sulfate and ammonium phosphate; ammonium salts of organic acids, e.g. ammonium fumarate and ammonium citrate; meat extract; yeast extract; corn steep liquor; casein hydrolyzate; urea as well as mixtures thereof. Furthermore various nutritional sources commonly used in the culture of microorganisms, such as inorganic salts, trace metal salts and vitamins, may be appropriately mixed and used in the present invention. In addition, materials effective in promoting the growth of the microorganism, in elevating the productivity of the target compound of the present invention or in maintaining the pH value of the medium on the desired level may be added, if required.

The pH value of the medium may be adjusted to 3.0 to 9.5, preferably 4 to 8. The culture may be carried out at a temperature of 20° to 45° C., preferably 25° to 37° C., either aerobically or anaerobically under conditions suitable for the growth of the microorganism for 5 to 120 hours, preferably about 12 to 72 hours.

The reduction may be effected by using the culture medium as such. Alternately, the cells may be separated by, for example, centrifugation, optionally washed and resuspended in a buffer solution or water. Then 4-hydroxy-2-butanone may be added to the suspension thus obtained. In this reaction, it is sometimes preferable to add a carbon source such as glucose or sucrose to the medium to thereby supply energy. The cells may be used as such in the form of viable cells. Alternately, they may be ground, treated with acetone or lyophilized. These cells, which have been optionally treated, may be immobilized prior to the use by a conventional method such as the polyacrylamide gel, sulfur-containing polysaccharide gel (such as carrageenan gel), alginic acid gel or agar gel method. Furthermore, an enzyme obtained from said treated cells by combining known methods may be used in the present invention.

The 4-hydroxy-2-butanone may be added either at once at the initiation of the reaction or in portions in the course of the reaction either as such, dissolved in water or an inert organic solvent or dispersed in, for example, a surfactant.

The reaction may be conducted at a pH value of 3 to 9, preferably 5 to 8, at 10° to 60° C., preferably 20° to 40° C. for 1 to 120 hours with or without stirring. The concentration of the substrate may preferably range from about 0.1 to 10%, though it is not restricted thereby.

The optically active 1,3-butanediol thus formed may be readily collected by extracting the reaction mixture, from which the cells may be optionally separated, with an organic solvent and purifying the extract by, for example, distillation or column chromatography.

EXAMPLES

The following Examples will further illustrate the present invention, which by no means limit the present invention.

In the following Examples, 1,3-butanediol in the reaction liquid mixture was easily determined according to gas chromatography [column: Thermon 3000, (2m), 130° C.] and the optical purity was determined by acetylating optically active 1,3-butanediol obtained by the reaction with acetyl chloride by an ordinary method and subjecting it to high performance liquid chromatography with an optical resolution column [column: Chiral cel OB (mfd. by Daicel Chemical Industries, Ltd.), solvent: n-hexane/2-propanol=19:1, wavelength: 220 nm, flow rate: 0.5 ml/min) [retention time: 15 min for (S)-enantiomer and 19.3 min for (R)-enantiomer].

Example 1

| <Microorganism-producing culture medium> | |
| --- | --- |
| glucose | 1.0% |
| yeast extract | 0.3% |
| peptone | 0.5% |
| 1,3-butanediol | 0.5% |
| $K_2HPO_4$ | 0.1% |
| $MgSO_4 \cdot 7H_2O$ | 0.05% |
| | pH 7.2 |

100 ml of the microorganism-producing culture medium having the above-described composition was put in a 500-ml Sakaguchi flask. After sterilization followed by inoculation with a microorganism shown in Table 1, the shaking culture was conducted at 30° C. for 48 h. Then the microorganism was separated by centrifugation and washed with physiological saline once to give viable cells.

Then 50 ml of distilled water was put in a 500-ml Sakaguchi flask, in which the microorganism obtained as described above was suspended. 0.5 g of racemic 1,3-butanediol was added to the suspension and the reaction was conducted under reciprocal shaking at 30° C. for 48 h.

After the completion of the reaction followed by removal of the cells by centrifugation, the supernatant liquid was saturated with sodium chloride and extracted with 50 ml of ethyl acetate. The ethyl acetate layer was analyzed according to gas chromatography to determine the amount of remaining 1,3-butanediol.

Thereafter ethyl acetate was dehydrated with anhydrous Glauber's salt. After removing the solvent, a syrup was obtained. The syrup was acetylated with acetyl chloride by an ordinary method and the product was dissolved in a solvent and analyzed according to high performance liquid chromatography to determine the absolute configuration and the optical purity of obtained 1,3-butanediol.

The results are shown in Table 1.

Example 2

*Candida parapsilosis* IFO 1396 was put in a 10-l jar fermenter containing 5 l of the same culture medium as that used in Example 1 and cultured under stirring at 250 r.p.m. at 30° C. for 24 h. The flow rate was 0.5 v.v.m. After the completion of the culture, the cells were collected by filtration, washed with 5 l of water and suspended in 500 ml of water. 10 g of racemic 1,3-butanediol was added to the suspension and the mixture was stirred at 30° C. for 48 h to conduct the reaction. After the completion of the reaction, the cells were removed by centrifugation. The obtained supernatant liquid was saturated with sodium chloride and extracted with 250 ml of ethyl acetate twice. The ethyl acetate layer was dehydrated with anhydrous Glauber's salt. After removing the solvent under reduced pressure, 4.2 g of a syrup was obtained. The syrup was distilled under reduced pressure to give 4.0 g of colorless transparent (R)-1,3-butanediol. The product had a specific rotatory power $[\alpha]_D^{20}$ of $-28°$ (C=1 in EtOH), an absolute configuration of the (R)-enantiomer and an optical purity determined by HPLC analysis of 96% e.e.

Example 3

*Geotrichum candidum* IFO 4601 was cultured and the reaction and extraction were conducted in the same manner as that of Example 2 to give 4.0 g of a syrup. 1,3-Butanediol thus obtained was analyzed to reveal that it had an absolute configuration of the (R)-enantiomer and an optical purity of 90% e.e.

Example 4

*Candida utilis* IFO 0639 was cultured and the reaction and extraction were conducted in the same manner as that of Example 2 to give 4.9 g of a syrup. 1,3-Butanediol thus obtained was analyzed to reveal that it had an absolute configuration of the (S)-enantiomer and an optical purity of 92% e.e.

Example 5

*Pichia opuntiae* var. *thermotolerans* IFO 10025 was cultured and the reaction and extraction were conducted in the same manner as that of Example 2 to give 3.7 g of a syrup. 1,3-Butanediol thus obtained was analyzed to reveal that it had an absolute configuration of the (S)-enantiomer and an optical purity of 97% e.e.

TABLE 1

| Microorganism | Amount of remaining 1,3-butanediol (mg/ml) | Absolute configuration | Optical purity of 1,3-butanediol (% e.e.) |
|---|---|---|---|
| *Brevibacterium iodinum* IFO 3558 | 2.4 | R | 51 |
| *Candida rugosa* IFO 1364 | 6.4 | R | 36 |
| *Candida parapsilosis* IFO 0640 | 5.8 | R | 50 |
| *Candida parapsilosis* IFO 0708 | 5.3 | R | 55 |
| *Candida parapsilosis* IFO 1396 | 4.0 | R | 98 |
| *Enterobacter cloacae* ATCC 7256 | 6.4 | R | 32 |
| *Geotrichum candidum* IFO 4601 | 1.9 | R | 94 |
| *Geotrichum candidum* IFO 5767 | 2.4 | R | 80 |
| *Geotrichum candidum* IFO 5368 | 2.6 | R | 98 |
| *Geotrichum retangulatum* JCM 1750 | 4.0 | R | 74 |
| *Geotrichum klebahnii* JCM 2171 | 5.0 | R | 58 |
| *Geotrichum fermentans* JCM 2467 | 4.0 | R | 88 |
| *Geotrichum capitatum* JCM 3908 | 5.5 | R | 40 |
| *Geotrichum eriense* JCM 3912 | 6.1 | R | 23 |
| *Klebsiella pneumonias* IFO 1209 | 5.5 | R | 30 |
| *Lodderomyces elongisporus* IFO 1676 | 4.9 | R | 72 |
| *Pseudomonas diminuta* IFO 12697 | 6.3 | R | 33 |
| *Rhodotorula glutinis* IFO 0395 | 6.0 | R | 34 |
| *Saccharomyces cerevisiae* AHU 3402 | 6.6 | R | 31 |
| *Saccharomycopsis lipolytica* IFO 1550 | 5.1 | R | 68 |
| *Sterigmatomyces elviae* DSM 70852 | 5.6 | R | 47 |
| *Trichosporon curtaneum* IFO 1198 | 4.8 | R | 67 |
| *Trichosporon capitatum* IFO 0743 | 5.5 | R | 35 |
| *Agrobacterium radiobacter* IFO 12664 | 5.5 | S | 40 |
| *Azotobacter chroococcum* IFO 12994 | 6.4 | S | 21 |
| *Bacillus brevis* IFO 3331 | 6.2 | S | 27 |
| *Bacillus cereus* AHU 1707 | 7.5 | S | 41 |
| *Bacillus cereus* AHU 1355 | 6.0 | S | 49 |
| *Bacillus sphaericus* IFO 3525 | 6.0 | S | 42 |
| *Bacillus sphaericus* IFO 3341 | 6.3 | S | 29 |
| *Bacillus subtilis* IFO 3007 | 5.9 | S | 54 |
| *Bacillus subtilis* IFO 3037 | 7.0 | S | 25 |
| *Bretfanomyces abstines* DSM 70726 | 6.8 | S | 29 |
| *Candida cariosilignicola* DSM 2148 | 5.2 | S | 70 |
| *Candida kefyr* (Beijerinck) DSM 70073 | 5.9 | S | 47 |
| *Candida krusei* (Castellani) DSM 70075 | 6.1 | S | 47 |
| *Candida succiphila* DSM 2149 | 6.5 | S | 50 |
| *Candida utilis* IFO 0639 | 4.3 | S | 91 |
| *Candida utilis* IFO 0626 | 4.9 | S | 76 |
| *Citrobacter freundii* AHU 1534 | 5.1 | S | 69 |
| *Corynebacterium glutamicum* ATCC 13032 | 6.9 | S | 21 |
| *Corynebacterium michiganense* IFO 13762 | 5.0 | S | 73 |
| *Dekkera bruxellensis* IFO 1590 | 5.9 | S | 32 |
| *Endomyces decipien* IFO 0102 | 6.8 | S | 21 |
| *Erwinia carotovora* subsp. *carotovora* IFO 3830 | 6.5 | S | 21 |

TABLE 1-continued

| Microorganism | Amount of remaining 1,3-butanediol (mg/ml) | Absolute configuration | Optical purity of 1,3-butanediol (% e.e.) |
|---|---|---|---|
| *Geotrichum fragrans* JCM 1749 | 6.0 | S | 31 |
| *Hansenula anomala* DSM 70130 | 2.4 | S | 26 |
| *Hansenula minuta* DSM 70274 | 4.6 | S | 58 |
| *Hansenula subpelliculosa* IFO 0808 | 4.4 | S | 71 |
| *Hansenula wickerhamii* DSM 70280 | 5.1 | S | 47 |
| *Hansenula wingei* DSM 10281 | 5.8 | S | 59 |
| *Issatchenkia scutulata* var. scutulata IFO 10070 | 6.8 | S | 46 |
| *Klebsiella pneumonias* IFO 12059 | 7.0 | S | 24 |
| *Kluyveromyces drosophilarum* IFO 1012 | 5.7 | S | 36 |
| *Kluyveromyces lactis* IFO 1267 | 4.9 | S | 76 |
| *Kluyveromyces lactis* IFO 1903 | 5.1 | S | 57 |
| *Micrococcus luteus* IFO 3333 | 7.0 | S | 21 |
| *Micrococcus roseus* IFO 3764 | 6.5 | S | 22 |
| *Mycobacterium smegmatis* IFO 3135 | 3.5 | S | 30 |
| *Pachysolen tannophilus* IFO 1007 | 6.4 | S | 25 |
| *Paracoccus denitrificans* IFO 12442 | 6.4 | S | 29 |
| *Pichia cellobiosa* DSM 2147 | 6.3 | S | 56 |
| *Pichia farinosa* IFO 1163 | 6.2 | S | 23 |
| *Pichia heedii* IFO 10020 | 6.5 | S | 40 |
| *Pichia heedii* IFO 10019 | 6.1 | S | 45 |
| *Pichia lindnerii* DSM 70718 | 7.1 | S | 40 |
| *Pichia opuntiae* var. thermotolerans IFO 10026 | 4.5 | S | 95 |
| *Pichia opuntiae* var. thermotolerans IFO 10025 | 4.4 | S | 97 |
| *Pichia pastoris* DSM 70382 | 6.0 | S | 59 |
| *Pichia querquum* DSM 70386 | 5.0 | S | 25 |
| *Pichia sargentensis* DSM 70388 | 3.9 | S | 28 |
| *Pichia trehalophia* DSM 70391 | 6.7 | S | 48 |
| *Protaminobacter ruber* IAM 1081 | 6.2 | S | 46 |
| *Pseudomonas acidovorans* IFO 13582 | 7.0 | S | 23 |
| *Pseudomonas diminuta* IFO 12697 | 4.2 | S | 51 |
| *Pseudomonas fluorescens* IFO 12055 | 5.5 | S | 52 |
| *Pseudomonas fluorescens* IFO 3081 | 6.2 | S | 40 |
| *Pseudomonas putida* IFO 3738 | 5.0 | S | 75 |
| *Saccharomyces cerevisiae* IAM 0216 | 6.6 | S | 24 |
| *Saccharomycopsis fibuligera* IFO 0103 | 5.3 | S | 22 |
| *Selenotila peltata* DSM 70579 | 5.6 | S | 45 |
| *Serratia marcescens* IAM 1105 | 6.9 | S | 23 |
| *Stephanoascus ciferrii* IFO 1854 | 4.2 | S | 78 |
| *Xanthomonas maltophilia* IFO 12690 | 5.1 | S | 41 |
| *Xanthomonasryzae* IAM 1657 | 6.2 | S | 34 |

Example 6

100 ml of a YM medium comprising 0.3% of yeast extract, 0.3% of malt extract, 0.5% of peptone and of glucose and having a pH of 6.0 in the case of yeast strains or 100 ml of a YMP medium comprising 2% of glucose, 0.5% of yeast extract, 0.3% of peptone, 0.3% of meat extract, 0.2% of $(NH_4)_2HPO_4$ and 0.1% of $KH_2PO_4$ and having a in the case of bacterial strains was put in a 500-ml Sakaguchi flask. After sterilization followed by the inoculation with a microorganism shown in Table 2, reciprocal shaking culture was conducted at 30° C. for 48 h. Cells were separated by centrifugation and washed once with physiological saline to give viable cells.

50 ml of distilled water was put in a 500-ml Sakaguchi flask and the viable cells obtained above was suspended therein. 5 g of glucose was added to the suspension. After the reciprocal shaking at 30° C. for 10 min, 0.5 g of 4-hydroxy-2-butanone was added thereto and the reaction was conducted under the reciprocal shaking at 30° C. for 20 h.

After the completion of the reaction, the cells were removed by centrifugation and the supernatant liquid thus obtained was saturated with sodium chloride. After extraction with 50 ml of ethyl acetate, the ethyl acetate layer was analyzed according to gas chromatography to determine the reaction yield.

Then the ethyl acetate layer was dehydrated with anhydrous Glauber's salt and the solvent was removed to give a syrup. The syrup was acetylated with acetyl chloride and dissolved in a solvent. The absolute configuration and optical purity of the product were determined according to high performance liquid chromatography. The results are shown in Table 2.

Example 7

*Candida utilis* IAM 4277 was put in a 10-l fermenter containing 5 l of a YM medium and cultured under stirring at 250 r.p.m. at 30° C. for 48 h. The flow rate was 0.5 v.v.m.

After the completion of the culture, the cells were collected by filtration, washed with 5 l of water and suspended in 500 ml of water. 5 g of 4-hydroxy-2-butanone and 50 g of glucose were added to the suspension and the mixture was stirred at 30° C. for 24 h to conduct the reaction.

After the completion of the reaction, the cells were removed by centrifugation. The obtained supernatant liquid was saturated with sodium chloride and extracted with 250 ml of ethyl acetate twice. The ethyl acetate layer was analyzed according to gas chromatography to reveal that the reaction yield was 85%.

Then the ethyl acetate layer was dehydrated with anhydrous Glauber's salt. After removing the solvent under reduced pressure, 4.0 g of a syrup was obtained. The syrup was distilled to give colorless transparent (R)-1,3-butanediol.

The absolute configuration and optical purity of the obtained 1,3-butanediol determined by HPLC were that of the (R)-enantiomer and 94% e.e., respectively.

Example 8

*Kluyveromyces lactis* IFO 1267 was cultured and the reaction and extraction were conducted in the same manner as that of Example 7 to give 4.5 g of a syrup. The reaction yield was 95%, and the absolute configuration and optical purity of the obtained 1,3-butanediol were that of the (R)-enantiomer and 92% e.e., respectively.

Example 9

*Candida parapsilosis* IFO 1396 was cultured and the reaction and extraction were conducted in the same manner as that of Example 7 to give 3.5 g of a syrup. The reaction yield was 64% and the absolute configuration and optical purity of the obtained 1,3-butanediol were that of the (S)-enantiomer and 98% e.e., respectively.

Example 10

*Geotrichum candidam* IFO 4601 was cultured and the reaction and extraction were conducted in the same manner as that of Example 7 to give 3.2 g of a syrup. The reaction yield was 78% and the absolute configuration and optical purity of the obtained 1,3-butanediol were that of the (S)-enantiomer and 88% e.e., respectively.

TABLE 2

| Microorganism | Reaction yield (%) | Absolute configuration | Optical purity (% e.e.) |
|---|---|---|---|
| *Ambrosiozyma cicatricosa* IFO 1846 | 46 | R | 48 |
| *Bacillus sereus* AHU 1355 | 25 | R | 55 |
| *Bacillus subtilis* IFO 3007 | 23 | R | 64 |
| *Candida cariosilignicola* DSM 2148 | 34 | R | 85 |
| *Candida arborea* IAM 4147 | 37 | R | 99 |
| *Candida kefyr* (Beijerinck) DSM 70073 | 43 | R | 54 |
| *Candida krusei* (Castellani) DSM 70075 | 41 | R | 59 |
| *Candida succiphila* DSM 2149 | 57 | R | 64 |
| *Candida utilis* IFO 0639 | 86 | R | 95 |
| *Candida utilis* IFO 0626 | 76 | R | 93 |
| *Candida utilis* IAM 4277 | 82 | R | 95 |
| *Citrobacter freundii* AHU 1534 | 54 | R | 69 |
| *Corynebacterium michiganense* IFO 13762 | 46 | R | 73 |
| *Hansenula polymorphs* ATCC 26012 | 96 | R | 85 |
| *Hansenula minuta* DSM 70274 | 34 | R | 45 |
| *Hansenula subpelliculosa* IFO 0808 | 56 | R | 76 |
| *Hansenula fabianii* IFO 1254 | 26 | R | 67 |
| *Hansenula wickerhamii* DSM 70280 | 43 | R | 45 |
| *Hansenula&ingei* DSM 10281 | 47 | R | 64 |
| *Issatchenkia scutulata* var. scutulata IFO 10070 | 45 | R | 99 |
| *Issatchenkia scutulata* IFO 10069 | 50 | R | 93 |
| *Kluyveromyces drosophilarum* IFO 1012 | 43 | R | 42 |
| *Kluyveromycesactis* IFO 1267 | 98 | R | 93 |
| *Kluyveromyces lactis* IFO 1903 | 88 | R | 92 |
| *Pichia cellohios* DSM 2147 | 76 | R | 79 |
| *Pichia heedii* IFO 10019 | 35 | R | 86 |
| *Pichia heedii* IFO 10020 | 24 | R | 81 |
| *Pichia lindnerii* DSM 70718 | 20 | R | 78 |
| *Pichia opuntiae* var. thermotolerans IFO 10025 | 54 | R | 94 |
| *Pichia pastoris* DSM 70382 | 58 | R | 87 |
| *Pichia trehalophia* DSM 70391 | 56 | R | 83 |
| *Protaminobacter ruber* IAM 1081 | 43 | R | 62 |
| *Pseudomonas diminuta* IFO 12697 | 42 | R | 65 |
| *Pseudomonas fluorescene* IFO 3081 | 53 | R | 76 |
| *Pseudomonas putida* IFO 3738 | 53 | R | 85 |
| *Stephanoascus ciferrii* IFO 1854 | 40 | R | 60 |
| *Rhodotorula rubra* IFO 0383 | 16 | R | 53 |
| *Selenotila peltata* DSM 70579 | 25 | R | 62 |
| *Schizosaccharomyces pombe* IFO 0363 | 25 | R | 35 |
| *Xanthomonas maltophilia* IFO 12690 | 34 | R | 59 |
| *Brevibacterium iodinum* IFO 3558 | 56 | S | 85 |
| *Candida rugosa* IFO 1364 | 53 | S | 63 |
| *Candida parapsilosis* IFO 0640 | 55 | S | 90 |
| *Candida parapsilosis* IFO 0708 | 51 | S | 94 |
| *Candida parapsilosis* IFO 1396 | 60 | S | 98 |

TABLE 2-continued

| Microorganism | Reaction yield (%) | Absolute configuration | Optical purity (% e.e.) |
|---|---|---|---|
| Geotrichum candidam IFO 4601 | 78 | S | 88 |
| Geotrichurt candidam IFO 5767 | 45 | S | 90 |
| Geotrichum candidam IFO 5368 | 65 | S | 93 |
| Geotrichum retangulatum JCM 1750 | 45 | S | 81 |
| Geotrichum klebahnii JCM 2171 | 54 | S | 75 |
| Geotrichum fermentans JCM 2467 | 48 | S | 77 |
| Geotrichum capitatum JCM 3908 | 44 | S | 81 |
| Geotrichum eriense JCM 3912 | 51 | S | 68 |
| Klebsiella pneumonias IFO 1209 | 32 | S | 30 |
| Lodderomyces elongisporus IFO 1676 | 62 | S | 70 |
| Saccharomycopsis lipolytica IFO 1550 | 61 | S | 65 |
| Trichosporon curtaneum IFO 1198 | 64 | S | 80 |
| Trichosporon capitatum IFO 0743 | 25 | 37 | |

It is claimed:

1. A process for producing optically active 1,3-butanediol which comprises (1) treating a mixture of 1,3-butanediol enantiomers with a microorganism capable of asymmetrically assimilating said mixture, leaving either the (R)- or the (S)-enantiomer intact, so as to produce optically active 1,3-butanediol, said microorganism to be selected from the group consisting of:

Brevibacterium iodinum
Candida parapsilosis
Enterobacter cloacae
Geotrichum candidum
Geotrichum rectangulatum
Geotrichum klebahnii
Geotrichum fermentans
Geotrichum capitatum
Geotrichum eriense
Lodderomyces elongisporus
Pseudomonas diminuta
Rhodotorula glutinis
Saccharomycopsis lipolytica
Trichosporon cutaneum
Agrobacterium radiobacter
Azotobacter chroococcum
Bacillus cereus
Bacillus subtilis
Brettanomyces abstines
Candida cariosilignicola
Candida kefyr (Beijerinck)
Candida krusei (Castellani)
Candida succiphila
Candida utilis
Citrobacter freundii
Corynebacterium glutamicum
Corynebacterium michiganense
Dekkera bruxellensis
Endomyces decipiens
Erwinia carotovora subsp. cartovora
Geotrichum fragrans
Hansenula anomala
Hansenula minuta
Hansenula subpelliculosa
Hansenula wickerhamii
Hansenula wingei
Issatchenkia scutulata var. scutulata
Klebsiella pneumoniae
Kluyveromyces lactis
Micrococcus luteus
Mycobacterium smegmatis
Pachysolen tannophilus
Paracoccus denitrificans
Pichia cellobiosa
Pichia lindnerii
Pichia opuntiae var. thermotolerans
Pichia pastoris
Pichia querquum
Pichia sargentensis
Pichia trehalophila
Pseudomonas diminuta
Pseudomonas putida
Selenotila peltata
Serratia marcescens
Stephanoascus ciferrii and
Xanthomonas maltophilia
and (2) collecting the optically active 1,3-butanediol remaining intact.

2. A process according to claim 1, wherein the microorganism is capable of leaving (R)-1,3 -butanediol intact, said organism being selected from the group consisting of:
Brevibacterium iodinum
Candida parapsilosis
Enterobacter cloacae
Geotrichum candidum
Geotrichum rectangulatum
Geotrichum klebahnii
Geotrichum fermentans
Geotrichum capitatum
Geotrichum eriense
Klebsiella pneumoniae
Lodderomyces elongisporus
Pseudomonas diminuta
Rhodotorula glutinis
Saccharomycopsis lipolytica and
Trichosporon cutaneum.

3. A process according to claim 2, wherein said microorganism has been immobilized.

4. A process according to claim 1, wherein the microorganism is capable of leaving (S)-1,3-butanediol intact, said organism being selected form the group consisting of:
Agrobacterium radiobacter
Azotobacter chroococcum
Bacillus cereus
Bacillus subtilis
Brettanomyces abstines
Candida cariosilignicola
Candida kefyr (Beijerinck)
Candida krusei (Castellani)
Candida succiphila
Candida utilis
Citrobacter freundii Corynebacterium glutamicum
Corynebacterium michiganense
Dekkera bruxellensis
Endomyces decipiens
Erwinia carotovora subsp. cartovora
Geotrichum fragrans
Hansenula anomala
Hansenula minuta
Hansenula subpelliculosa
Hansenula wickerhamii
Hansenula wingei
Issatchenkia scutulata var. scutulata
Klebsiella pneumoniae
Kluyveromyces lactis
Micrococcus luteus
Mycobacterium smegmatis
Pachysolen tannophilus
Paracoccus denitrificans
Pichia cellobiosa
Pichia lindnerii
Pichia opuntiae var. thermotolerans
Pichia pastoris
Pichia querquum
Pichia trehalophila
Pseudomonas diminuta
Pseudomonas putida
Selenotila peltata
Serratia marcescens
Stephanoascus ciferrii and
Xanthomonas maltophilia.

5. A process according to claim 4, wherein said microorganism has been immobilized.

6. A process according to claim 1, wherein said microorganism has been immobilized.

7. A process for producing optically active 1,3-butanediol which comprises (1) treating a mixture of 1,3-butanediol enantiomers with a microorganism capable of asymmetrically assimilating said mixture, leaving either the (R)- or the (S)-enantiomer intact to produce optically active 1,3-butanediol, said microorganism to be selected from the group consisting of:
Brevibacterium iodinum
Klebsiella pneumoniae
Lodderomyces elongisporus
Pseudomonas diminuta
Pseudomonas putida
Rhodotorula glutinis
Saccharomycopsis lipolytica
Trichosporon cutaneum
Agrobacterium radiobacter
Azotobacter chroococcum
Bacillus subtilis
Corynebacterium michiganense
Dekkera bruxellensis
Endomyces decipiens
Erwinia carotovora subsp. cartovora
Hansenula subpelliculosa
Issatchenkia scutulata var. scutulata
Micrococcus luteus
Mycobacterium smegmatis
Pachysolen tannophilus
Paracoccus denitrificans
Stephanoascus ciferrii and
Xanthomonas maltophilia
and (2) collecting the optically active 1,3-butanediol remaining intact.

8. A process according to claim 7, wherein said microorganism has been immobilized.

9. A process for producing optically active 1,3-butanediol which comprises (1) treating a mixture of 1,3-butanediol enantiomers with a microorganism, capable of asymmetrically assimilating said mixture, said microorganism to be selected from the group consisting of:

| Organism | Collection | Number |
|---|---|---|
| Brevibacterium iodinum | IFO | 3558 |
| Candida parapsilosis | IFO | 1396 |
| Enterobacter cloacae | ATCC | 7256 |
| Geotrichum candidum | IFO | 5368 |
| Geotrichum rectangulatum | JCM | 1750 |
| Geotrichum klebahnii | JCM | 2171 |
| Geotrichum fermentans | JCM | 2467 |
| Geotrichum capitatum | JCM | 3908 |
| Geotrichum eriense | JCM | 3912 |
| Klebsiella pneumoniae | IFO | 12009 |
| Lodderomyces elongisporus | IFO | 1676 |
| Pseudomonas diminuta | IFO | 12697 |
| Rhodotorula glutinis | IFO | 0395 |
| Saccharomycopsis lipolytica | IFO | 1550 |
| Trichosporon cutaneum | IFO | 1198 |
| Agrobacterium radiobacter | IFO | 12664 |
| Azotobacter chroococcum | IFO | 12994 |
| Bacillus cereus | AHU | 1707 |
| Bacillus subtilis | IFO | 3007 |
| Brettanomyces abstines | DSM | 70726 |
| Candida cariosilignicola | DSM | 2148 |
| Candida kefyr (Beijerinck) | DSM | 70073 |
| Candida krusei (Castellani) | DSM | 70075 |
| Candida succiphila | DSM | 2149 |
| Candida utilis | IFO | 0639 |
| Citrobacter freundii | AHU | 1534 |
| Corynebacterium glutamicum | ATCC | 13032 |
| Corynebacterium michiganense | IFO | 13762 |
| Dekkera bruxellensis | IFO | 1590 |
| Endomyces decipiens | IFO | 0102 |
| Erwinia carotovora subsp. cartovora | IFO | 3830 |
| Geotrichum fragrans | JCM | 1749 |
| Hansenula anomala | DSM | 70130 |
| Hansenula minuta | DSM | 70274 |
| Hansenula subpelliculosa | IFO | 0808 |
| Hansenula wickerhamii | DSM | 70280 |
| Hansenula wingei | DSM | 10281 |
| Issatchenkia scutulata var. scutulata | IFO | 10070 |
| Klebsiella pneumoniae | IFO | 12059 |
| Kluyveromyces lactis | IFO | 1267 |
| Micrococcus luteus | IFO | 3333 |
| Mycobacterium smegmatis | IFO | 3135 |
| Pachysolen tannophilus | IFO | 1007 |
| Paracoccus denitrificans | IFO | 12442 |
| Pichia cellobiosa | DSM | 2147 |
| Pichia lindnerii | DSM | 70718 |
| Pichia opuntiae var. thermotolerans | IFO | 10025 |
| Pichia pastoris | DSM | 70382 |
| Pichia querquum | DSM | 70386 |
| Pichia sargentensis | DSM | 70388 |
| Pichia trehalophila | DSM | 70391 |
| Pseudomonas putida | IFO | 3738 |
| Selenotila peltata | DSM | 70579 |
| Serratia marcescens | IAM | 1105 |
| Stephanoascus ciferrii | IFO | 1854 and |
| Xanthomonas maltophilia | IFO | 12690 | and (2) collecting the optically active 1,3-butanediol remaining intact.

10. A process according to claim 9, wherein the microorganism is capable of leaving (R)-1,3-butanediol intact, said organism being selected from the group consisting of:

| Organism | Collection | Number |
|---|---|---|
| Brevibacterium iodinum | IFO | 3558 |
| Candida parapsilosis | IFO | 1396 |
| Enterobacter cloacae | ATCC | 7256 |
| Geotrichum candidum | IFO | 5368 |

| | | |
|---|---|---|
| -continued | | |
| Geotrichum rectangulatum | JCM | 1750 |
| Geotrichum klebahnii | JCM | 2171 |
| Geotrichum fermentans | JCM | 2467 |
| Geotrichum capitatum | JCM | 3908 |
| Geotrichum eriense | JCM | 3912 |
| Klebsiella pneumoniae | IFO | 12009 |
| Lodderomyces elongisporus | IFO | 1676 |
| Pseudomonas diminuta | IFO | 12697 |
| Rhodotorula glutinis | IFO | 0395 |
| Saccharomycopsis lipolytica | IFO | 1550 and |
| Trichosporon curtaneum | IFO | 1198. |

11. A process according to claim 9, wherein the microorganism is capable of leaving (S)-1,3-butanediol intact, said organism being selected form the group consisting of:

| | | |
|---|---|---|
| Agrobacterium radiobacter | IFO | 12664 |
| Azotobacter chroococcum | IFO | 12994 |
| Bacillus cereus | AHU | 1355 |
| Bacillus subtilis | IFO | 3007 |
| Brettanomyces abstines | DSM | 70726 |
| Candida cariosilignicola | DSM | 2148 |
| Candida kefyr (Beijerinck) | DSM | 70073 |
| Candida krusei (Castellani) | DSM | 70075 |
| Candida succiphila | DSM | 2149 |
| Candida utilis | IFO | 0639 |
| Citrobacter freundii | AHU | 1534 |
| Corynebacterium glutamicum | ATCC | 13032 |
| Corynebacterium michiganense | IFO | 13762 |
| Dekkera bruxellensis | IFO | 1590 |
| Endomyces decipiens | IFO | 0102 |

| | | |
|---|---|---|
| -continued | | |
| Erwinia carotovora subsp. catovora | IFO | 3830 |
| Geotrichum fragrans | JCM | 1749 |
| Hansenula anomala | DSM | 70130 |
| Hansenula minuta | DSM | 70274 |
| Hansenula subpelliculosa | IFO | 0808 |
| Hansenula wickerhamii | DSM | 70280 |
| Hansenula wingei | DSM | 10281 |
| Issatchenkia scutulata var. scutulata | IFO | 10070 |
| Klebsiella pneumoniae | IFO | 12059 |
| Kluyveromyces lactis | IFO | 1267 |
| Micrococcus luteus | IFO | 3333 |
| Mycobacterium smegmatis | IFO | 3135 |
| Pachysolen tannophilus | IFO | 1007 |
| Paracoccus denitrificans | IFO | 12442 |
| Pichia cellobiosa | DSM | 2147 |
| Pichia lindnerii | DSM | 70718 |
| Pichia opuntiae var. thermotolerans | IFO | 10025 |
| Pichia pastoris | DSM | 70382 |
| Pichia querquum | DSM | 70386 |
| Pichia sargentensis | DSM | 70388 |
| Pichia trehalodhila | DSM | 70391 |
| Pseudomonas diminuta | IFO | 12697 |
| Pseudomonas putida | IFO | 3738 |
| Selenotila peltata | DSM | 70579 |
| Serratia marcescens | IAM | 1105 |
| Stephanoascus ciferrii | IFO | 1854 and |
| Xanthomonas maltophilia | IFO | 12690. |

12. A process according to claim 9, wherein said microorganism has been immobilized.

13. A process according to claim 9, wherein said microorganism is collected, washed and resuspended in water or a buffer.

* * * * *